(12) United States Patent
Hu (10) Patent No.: US 6,743,593 B2
(45) Date of Patent: Jun. 1, 2004

(54) IMMUNOLOGICAL METHODOLOGY FOR DISCERNING HUMAN PAPILLOMAVIRUS

(75) Inventor: Yao Xiong Hu, Murray, UT (US)

(73) Assignee: Impact Diagnostics, Inc., Salt Lake City, UT (US)

( * ) Notice: Subject to any disclaimer, the term of this patent is extended or adjusted under 35 U.S.C. 154(b) by 0 days.

(21) Appl. No.: 09/828,645

(22) Filed: Apr. 5, 2001

(65) Prior Publication Data

US 2003/0027750 A1 Feb. 6, 2003

Related U.S. Application Data

(60) Provisional application No. 60/194,796, filed on Apr. 5, 2000.

(51) Int. Cl.$^7$ ............................................. G01N 33/53
(52) U.S. Cl. ........................................ 435/7.1; 435/7.94
(58) Field of Search ................................ 435/7.1, 7.94, 435/6, 69.1; 424/204.1, 186.1; 530/328.3

(56) References Cited

U.S. PATENT DOCUMENTS

| 4,777,239 A | * 10/1988 | Schoolnik et al. ........ 530/326 |
| 5,629,161 A | 5/1997 | Muller et al. |
| 5,932,412 A | 8/1999 | Dillner et al. |

FOREIGN PATENT DOCUMENTS

| EP | 0 344 940 A2 | 12/1989 |
| WO | WO 87/01375 | * 3/1987 |
| WO | WO 91/18294 | 11/1991 |

OTHER PUBLICATIONS

Nobbenhuis et al.; "Relation of human papillomavirus status to certical lesions and consequences for cervical–cancer screening; a prospective study"; *Lancet* 354–20–25, 1999.
Cuzick et al.; "A systematic review of the role of human papilloma virus (HPV) testing . . . "; *British Journal of Cancer* 83:561–565, 2000.
Pirog et al.; "Prevalence of Human Papillomavirus DNA in Different Histological . . . "; *American Journal of Pathology* 156:1055–1062, 2000.

Frisch et al.; "Human Papillomavirus–Associated Carcinomas in Hawaii and the Mainland U.S."; *Cancer* 88:1464–1469, 2000.
Gregoire, et al.; "Preferential Association of Human Papillomavirus With High–Grade Histologic . . . "; *Journal of the National Cancer Institute* 87:1705–1709, 1995.
Mellin et al.; "Human papillomavirus (HPV) DNA in tonsillar cancer . . . " *International Journal of Cancer* 89: 300–304, 2000.
Zumbach et al.; "Antibodies against oncoproteins E6 and E7 . . . " *International Journal of Cancer* 85:815–818, 2000.
Dréau et al.; "Human Papilloma Virus in Melanoma Biopsy . . . " *Annals of Surgery* 231:664–671, 2000.
Soini et al.; "Presence of human papillomavirus DNA and abnormal p53 protein . . . "; *Thorax* 51:887–893, 1996.
Sugase et al.; "Distinct manifestations of human papilloma viruses in the vagina"; *International Journal of Cancer* 72: 412–415,1997.
Sun et al.; "Serum Antibodies to Human Papillomavirus 16 Proteins . . . " *Cancer Epidemiology, Biomarkers & Prevention* 8:935–940,1999.
Meschede et al.; "Antibodies Against Early Proteins of Human Papillomaviruses . . . "; *Journal of Clinical Microbiology* 36:475–480.
Petter et al.; Specific serum IgG, IgM and IgA antibodies to human papillomavirus types y, 11, 16, 18 and 31 . . . ; *Journal of General Virology* 81: 701–708; 2000.

* cited by examiner

*Primary Examiner*—Ali R. Salimi
(74) *Attorney, Agent, or Firm*—Pate & Pierce & Baird (57) ABSTRACT

The invention provides peptides designed to be highly reactive with antibodies from patients infected with oncogenic HPV. Also disclosed is a method for their use in an immunoassay to detect HPV infection and HPV associated epithelial cell abnormalities, most notably those associated with premalignant and malignant epithelial cell lesions. The peptides and the disclosed method are particularly useful for diagnosing carcinomas of the uterine cervix, or pre-stages thereof, or those at risk of development of carcinoma. The detection can be effected on blood samples, or other bodily fluid or tissue, by ascertaining the presence of IgA or IgG antibodies against HPV 16 and/or 18.

4 Claims, 5 Drawing Sheets

| SYMBOL | AMINO ACID |
| --- | --- |
| Y | L-tyrosine |
| G | glycine |
| F | L-phenylalanine |
| M | L-methionine |
| A | L-alanine |
| S | L-serine |
| I | L-isoleucine |
| L | L-leucine |
| T | L-threonine |
| V | L-valine |
| P | L-proline |
| K | L-lysine |
| H | L-histidine |
| Q | L-glutamine |
| E | L-glutamic acid |
| W | L-tryptophan |
| R | L-arginine |
| D | L-aspartic acid |
| N | L-asparagine |
| C | L-cysteine |

FIG. 1

SEQ ID. NO. 1 =
N-terminal D I C N T M H Y T N W T H I Y I C E E C-terminal

SEQ ID. NO. 2 =
N-terminal H K S A I V T L T Y D S E W Q R C-terminal

SEQ. ID. NOs. 1 and 2, denoted by underlining, are attributed to the E2 coding region of HPV-16 as follows::

|     | 5 | | | | 10 | | | | 15 | | | | 20 | | | | 25 | | | | 30 | | | | | | | | | |
| --- | - | - | - | - | -- | - | - | - | -- | - | - | - | -- | - | - | - | -- | - | - | - | -- | - | - | - | - | - | - | - | - | - |
| 1   | M | E | T | L | C | Q | R | L | N | V | C | Q | D | K | I | L | T | H | Y | E | N | D | S | T | D | L | R | D | H | I |
| 31  | D | Y | W | K | H | M | R | L | E | C | A | I | Y | Y | K | A | R | E | M | G | F | K | H | I | N | H | Q | V | V | P |
| 61  | T | L | A | V | S | K | N | K | A | L | Q | A | I | E | L | Q | L | T | L | E | T | I | Y | N | S | Q | Y | S | N | E |
| 91  | K | W | T | L | Q | D | V | S | L | E | V | Y | L | T | A | P | T | G | C | I | K | K | H | G | Y | T | V | E | V | Q |
| 121 | F | D | G | D | I | C | N | T | M | H | Y | T | N | W | T | H | I | Y | I | C | E | E | A | S | V | T | V | V | E | G |
| 151 | Q | V | D | Y | Y | G | L | Y | Y | V | H | E | G | I | R | T | Y | F | V | Q | F | K | D | D | A | E | K | Y | S | K |
| 181 | N | K | V | W | E | V | H | A | G | G | Q | V | I | L | C | P | T | S | V | F | S | S | N | E | V | S | S | P | E | I |
| 211 | I | R | Q | H | L | A | N | H | P | A | A | T | H | T | K | A | V | A | L | G | T | E | E | T | Q | T | T | I | Q | R |
| 241 | P | R | S | E | P | D | T | G | N | P | C | H | T | T | K | L | L | H | R | D | S | V | D | S | A | P | I | L | T | A |
| 271 | F | N | S | S | H | K | G | R | I | N | C | N | S | T | T | P | I | V | H | L | K | G | D | A | N | T | L | K | C |   |
| 301 | L | R | Y | R | F | K | K | H | C | T | L | Y | T | A | V | S | S | T | W | H | W | T | G | H | N | V | K | H | K | S |
| 331 | A | I | V | T | L | T | Y | D | S | E | W | Q | R | D | Q | F | L | S | Q | V | K | I | P | K | T | I | T | V | S | T |
| 361 | G | F | M | S | I | | | | | | | | | | | | | | | | | | | | | | | | | |

FIG. 2

SEQ ID. NO. 3 =
N-terminal P T L H E Y M L D L Q P E T T D L Y C Y E Q L N D S S E E E C-terminal SEQ ID. NO. 4 =
N-terminal C D S T L R L C V Q S T H V D I R T L E C-terminal Sequence ID. NOs. 3 and 5, denoted by underlining, are attributed to the E7 coding region of HPV-16 as follows:

SEQ ID. NO. 5 =

N-terminus E K T G I L T V T Y H S E T Q R T K F C-terminus

SEQ ID. NO. 5, denoted by underlining, is attributed to the E2 coding region of HPV-18 as follows:

TABLE I. Serum Immunoassays Employing Peptides of Invention. These assays are compared against Pap cytology and HPV DNA Hybrid Capture analyses of cervical cells from the same patients. Serum and cervical cells were taken from participants by a gynecological physician. Pap smears and the Digene HPV DNA Assays[1] were processed at a certified clinical laboratory. Prior to completion of this trial, persons doing the Impact Diagnostics HPV Immunoassay were not informed of the results of other assays or of participant histories. Unless otherwise specified, participants were more than 35 years old. *KEY*: pos = positive; neg = negative; n/a = not applicable or not done; insufficient = insufficient number of cells for analysis

| Sample | Pap Smear | Digene HPV DNA Assay | Impact HPV Immunoassay[2] | | | | Comments |
|---|---|---|---|---|---|---|---|
| | | | HPV-16a | HPV-16b | HPV-18 | | |
| 1 | neg | n/a | pos | pos | neg | | CERVICAL CANCER diagnosed in 1987; surgical removal of lesion |
| 2 | n/a | n/a | pos | pos | pos | | CERVICAL CANCER diagnosed in 1991; total hysterectomy |
| 3 | neg | neg | pos | neg | pos | | Previous Pap Smear -- CIN III[3] |
| 4 | neg | neg | pos | neg | pos | | Previous Pap Smear -- CIN III[3] |
| 5 | neg | Insufficient | neg | neg | pos | | Previous Pap Smear -- CIN I[3] |
| 6 | neg | neg | neg | pos | pos | | Previous Pap Smear -- CIN I[3] |
| 7 | neg | neg | pos | neg | pos | | Previous Pap Smear -- CIN I[3] |
| 8 | neg | neg | pos | neg | pos | | Previous Pap Smear -- CIN I[3] |
| 9 | neg | neg | neg | neg | pos | | Previous Pap Smear -- CIN I-II[3] |
| 10 | neg | neg | pos | pos | neg | | No history of abnormal Pap Smears; multiple sex partners confirmed |
| 11 | neg | neg | pos | pos | pos | | No history of abnormal Pap Smears; multiple sex partners confirmed |
| 12 | neg | neg | pos | pos | pos | | No history of abnormal Pap Smears |
| 13 | neg | neg | pos | neg | neg | | No history of abnormal Pap Smears |
| 14 | neg | neg | neg | pos | pos | | No history of abnormal Pap Smears |
| 15 | ASCUS[3] | pos | pos | pos | neg | | No history of abnormal Pap Smears |
| 16 | neg | neg | neg | neg | neg | | No history of abnormal Pap Smears |
| 17 | n/a | n/a | pos | neg | neg | | Promiscuous woman |
| 18 | n/a | n/a | pos | neg | neg | | Promiscuous woman |
| 19 | neg | neg | neg | neg | neg | | Virgin -- 14 years old |
| 20 | neg | neg | neg | neg | neg | | Virgin -- 15 years old |
| 21 | neg | n/a | neg | neg | neg | | No history of abnormal Pap Smears; multiple sex partners confirmed |
| 22 | neg | neg | neg | neg | neg | | No history of abnormal Pap Smears |
| 23 | neg | neg | neg | neg | neg | | No history of abnormal Pap Smears |
| 24 | neg | neg | neg | neg | neg | | No history of abnormal Pap Smears |

FIG. 5

TABLE 1. Serum Immunoassays Employing Peptides of Invention. Continued

| Sample | Pap Smear | Digene HPV DNA Assay | Impact HPV Immunoassay[2] | | | Comments |
|---|---|---|---|---|---|---|
| | | | HPV-16a | HPV-16b | HPV-18 | |
| 25 | neg | neg | neg | neg | neg | No history of abnormal Pap Smears |
| 26 | neg | neg | neg | neg | neg | No history of abnormal Pap Smears |
| 27 | neg | neg | neg | neg | neg | No history of abnormal Pap Smears |
| 28 | neg | neg | neg | neg | neg | No history of abnormal Pap Smears |
| 29 | neg | neg | neg | neg | neg | No history of abnormal Pap Smears |
| 30 | neg | neg | neg | neg | neg | No history of abnormal Pap Smears |
| 31 | neg | neg | neg | neg | neg | No history of abnormal Pap Smears |

[1] The Digene HPV DNA Assay requires a substantial number of cells for successful detection of HPV DNA. Also, it only finds HPV DNA when the virus is abundantly proliferating (and not when infections are dormant).

[2] HPV-16a = Epitope for the E2 Region of HPV-16; HPV-16b = Epitope for the E7 Region of HPV-16; HPV-18 = Epitope for the E2 Region of HPV-18. For the HPV Immunoassay, a positive result is visually expressed by a prominent BLUE color and a negative one by remaining COLORLESS.

[3] ASCUS refers to unusual or atypical cells in a Pap Smear. These are usually of undetermined significance and most often turn out to be inconsequential. In *mild dysplasia* (CIN I), only a few cells are abnormal, while in *moderate dysplasia* (CIN II) the abnormal cells involve about one-half of the thickness of the surface lining of the cervix. In *severe dysplasia* or *carcinoma-in-situ* (CIN III), the entire thickness of cells is disordered, but the abnormal cells have not yet spread below the surface. Carcinoma-in-situ means "cancer in place". If this condition is not treated, it often will grow into *invasive cancer*. In dysplasia and carcinoma-in-situ all of the abnormalities are confined to the surface lining (or "skin") of the cervix. For invasive cancer, the cells are not only disordered throughout the entire thickness of the lining, but they invade the tissue underlying the surface.

SEQUENCE LISTING

<160> NUMBER OF SEQ ID NOS: 8

<210> SEQ ID NO 1
<211> LENGTH: 19
<212> TYPE: PRT
<213> ORGANISM: Artificial Sequence
<220> FEATURE:
<223> OTHER INFORMATION: Derived from theE2 early region of HPV-16

<400> SEQUENCE: 1

Asp Ile Cys Asn Thr Met His Tyr Thr Asn Trp Thr His Ile Tyr Ile
1               5                   10                  15

Cys Glu Glu

<210> SEQ ID NO 2
<211> LENGTH: 16
<212> TYPE: PRT
<213> ORGANISM: Artificial Sequence
<220> FEATURE:
<223> OTHER INFORMATION: Derived from the E2 early region of HPV-16

```
<400> SEQUENCE: 2

His Lys Ser Ala Ile Val Thr Leu Thr Tyr Asp Ser Glu Trp Gln Arg
1               5                   10                  15

<210> SEQ ID NO 3
<211> LENGTH: 30
<212> TYPE: PRT
<213> ORGANISM: Artificial Sequence
<220> FEATURE:
<223> OTHER INFORMATION: Derived from the E7 early region of HPV-16

<400> SEQUENCE: 3

Pro Thr Leu His Glu Tyr Met Leu Asp Leu Gln Pro Glu Thr Thr Asp
1               5                   10                  15

Leu Tyr Cys Tyr Glu Gln Leu Asn Asp Ser Ser Glu Glu Glu
            20                  25                  30

<210> SEQ ID NO 4
<211> LENGTH: 20
<212> TYPE: PRT
<213> ORGANISM: Artificial Sequence
<220> FEATURE:
<223> OTHER INFORMATION: Derived from the E7 early region of HPV-16

<400> SEQUENCE: 4

Cys Asp Ser Thr Leu Arg Leu Cys Val Gln Ser Thr His Val Asp Ile
1               5                   10                  15

Arg Thr Leu Glu
            20

<210> SEQ ID NO 5
<211> LENGTH: 19
<212> TYPE: PRT
<213> ORGANISM: Artificial Sequence
<220> FEATURE:
<223> OTHER INFORMATION: Derived from the E2 early region of HPV-18

<400> SEQUENCE: 5

Glu Lys Thr Gly Ile Leu Thr Val Thr Tyr His Ser Glu Thr Gln Arg
1               5                   10                  15

Thr Lys Phe

<210> SEQ ID NO 6
<211> LENGTH: 19
<212> TYPE: PRT
<213> ORGANISM: Artificial Sequence
<220> FEATURE:
<223> OTHER INFORMATION: Derived from the E2 early region of HPV-16
<221> NAME/KEY: MISC_FEATURE
<222> LOCATION: (3)..(3)
<223> OTHER INFORMATION: Xaa = L-Carboxymethylcysteine
<221> NAME/KEY: MISC_FEATURE
<222> LOCATION: (17)..(17)
<223> OTHER INFORMATION: Xaa = L-Carboxymethylcysteine

<400> SEQUENCE: 6

Asp Ile Xaa Asn Thr Met His Tyr Thr Asn Trp Thr His Ile Tyr Ile
1               5                   10                  15

Xaa Glu Glu

<210> SEQ ID NO 7
<211> LENGTH: 30
<212> TYPE: PRT
<213> ORGANISM: Artificial Sequence
```

```
-continued

<220> FEATURE:
<223> OTHER INFORMATION: Derived from the E7 early region of HPV-16
<221> NAME/KEY: misc_feature
<222> LOCATION: (19)..(19)
<223> OTHER INFORMATION: Xaa = L-carboxymethylcysteine

<400> SEQUENCE: 7

Pro Thr Leu His Glu Tyr Met Leu Asp Leu Gln Pro Glu Thr Thr Asp
1               5                   10                  15

Leu Tyr Xaa Tyr Glu Gln Leu Asn Asp Ser Ser Glu Glu Glu
            20                  25                  30

<210> SEQ ID NO 8
<211> LENGTH: 20
<212> TYPE: PRT
<213> ORGANISM: Artificial Sequence
<220> FEATURE:
<223> OTHER INFORMATION: Derived from the E7 early region E7  of HPV-16
<221> NAME/KEY: misc_feature
<222> LOCATION: (1)..(1)
<223> OTHER INFORMATION: Xaa = L-carboxymethylcysteine
<221> NAME/KEY: misc_feature
<222> LOCATION: (8)..(8)
<223> OTHER INFORMATION: Xaa = L-carboxymethylcysteine

<400> SEQUENCE: 8

Xaa Asp Ser Thr Leu Arg Leu Xaa Val Gln Ser Thr His Val Asp Ile
1               5                   10                  15

Arg Thr Leu Glu
            20
```

IMMUNOLOGICAL METHODOLOGY FOR DISCERNING HUMAN PAPILLOMAVIRUS

RELATED APPLICATION

This application claims the benefit of provisional application Serial No. 60/194,796, filed Apr. 5, 2000, and entitled "Immunological Methodology for Discerning Human Papillomavirus."

BACKGROUND OF THE INVENTION

1. Field

The present invention relates generally to the field of peptides reactive with antibodies directed against HPV. Some have termed this type of peptide as antigenic or immunoreactive. More particularly, the invention relates to peptides derived from the early coding region of the E2, E6, and E7 oncoproteins of human papillomavirus [HPV] and a method for their use for the diagnosis of HPV associated epithelial cell abnormalities via an immunoassay.

2. State of the Art

The human papillomaviruses (HPV), named because certain types induce warts or papillomas, cause virtually all cervical cancers (Nobbenhuis et al., "Relation of human papillomavirus status to cervical lesions and consequences for cervical-cancer screening: a prospective study", The Lancet, 354:20–25, 1999; Cuzick et al., "A systematic review of the role of human papilloma virus (HPV) testing within a cervical screening programme: summary and conclusions", British Journal of Cancer, 83:561–565, 2000). These encompass not only squamous cell carcinomas (Nobbenhuis et al., 1999) but also adenocarcinomas (Pirog et al., "Prevalence of human papillomavirus DNA in different histological subtypes of cervical adenocarcinoma," American Journal of Pathology, 157:1055–1062, 2000). These viruses are also strongly associated with vulvar and vaginal carcinomas (Frisch et al., "Human papillomavirus-associated carcinomas in Hawaii and the mainland US", Cancer 88:1464–1469, 2000; Sugase et al., "Distinct manisfestations of human papillomaviruses in the vagina", International Journal of Cancer, 72:412–415, 1997), as well as cancers of the anus (Frisch et al., 2000) and penis (Gregoire et al., "Preferential association of human papillomavirus with high-grade histologic variants of penile-invasive squamous cell carcinoma", Journal of the National Cancer Institute, 87:1705–1709,1995). Moreover, HPV may be responsible for certain carcinomas in the head and neck region (Mellin et al., "Human papillomavirus (HPV) DNA in tonsillar cancer: clinical correlates, risk of relapse, and survival", International Journal of Cancer, 89:300–304, 2000; Zumbach et al., "Antibodies against oncoproteins E6 and E7 of human papillomavirus types 16 and 18 in patients with head-and-neck squamous-cell carcinoma", International Journal of Cancer, 85:815–818, 2000), seem associated with the more deadly melanomas (Dreau et al., "Human papilloma virus in melanoma biopsy specimens and its relations to melanoma progression", Annals of Surgery, 231:664–671, 2000), and could play a role in lung carcinomas (Soini et al., "Presence of human papillomavirus DNA and abnormal p53 protein accumulation in lung carcinoma", Thorax 51:887–893, 1996) and perhaps other cancers. HPV exist as different genetic types, designated by numbers, concerning which only a subset is oncogenic or cancer causing. Over 100 HPV genotypes have been identified. Cancers stem overwhelmingly from HPV 16 and 18 but also from types 31, 33, 35, 45, 51, 52, 56 and 58. The virus infects cervical and other cells that can support virus propagation, where it causes abnormal cellular changes that can lead to life threatening malignancies. Cervical cancer is the second most common cancer among women worldwide. Each year, about 450,000 women worldwide are diagnosed with cervical cancer, and nearly 300,000 women die of this disease. Since the advent of organized cervical cancer screening via cytology 50 years ago, the mortality rate of cervical cancer has dramatically decreased in developed countries. In fact, cervical cancer can be considered preventable. The key to prevention is the timely identification and management of precancerous lesions through accessible and affordable screening programs. At present, 11.8% of global cancer incidence in females is due to HPV infections of the cervix. There is consensus that oncogenic HPV detection would be an effective way to identify cancer victims or those at high risk for the disease. Notably, HPV detection would facilitate early detection, when cancer would exist at a more readily curable stage.

HPV infection requires cells able to replicate their DNA, specifically those in the basal epidermal layer. Entry occurs through microlesions that expose basal proliferating cells to the surface. The virus attaches to a cell surface receptor and gains entry into the cytosol. The infecting virus particle contains a closed-circular double-stranded DNA genome of 7000 to 8000 base pairs composed of eight early transcribed open reading frames, E1 to E8, which are unequally represented among HPV genotypes, two late open reading frames, and a noncoding long control region.

Much has been discovered about how HPV DNA integrates into host chromosomes and how the E1 and E2 oncoproteins are involved with this process. Its relevance to immunological diagnostics is that antibodies against E1 and E2 gene products comprise evidence that HPV infection has occurred.

The manner by which infection by HPV leads to cancer centers about the E6 and E7 gene products. In host cells, these form complexes with the cellular p53 and retinoblastoma tumor suppressing proteins regulating cell division. By functionally neutralizing or inactivating these proteins, cells enter into the S phase of the cell cycle. The E7 oncoprotein further destabilizes cell control through its interaction with the cyclin-dependent kinase inhibitor protein, p21. These interactions set the stage for controlling host cell proliferation and differentiation (i.e., transformation), a first step in the conversion of normal cells to preneoplastic ones and ultimately to the full expression of malignancy.

The E6 and E7 oncoproteins are constitutively expressed in tumor cells, and silencing these genes yields reversion of the malignant phenotype. Thus, the E6 and E7 gene products seem tumor-specific antigens, and possible targets or probes for antibodies in immunological cancer tests as well as antigens in vaccines for controlling HPV induced tumors.

Indeed, the E6 and E7 oncoproteins appear natural targets for antibody production due to their consistent expression in cervical cancer cells. The response against the E7 one in earlier studies had only been moderately disease specific, but E7 IgG and IgA have now been verified as strongly disease associated. Antibodies against the E6 and E7 oncoproteins are at high levels in sera from cervical cancer patients compared against non-cancer controls. Moreover, such antibodies seem detectable by immunological means even when present in lesser amounts. Sensitivity for identifying HPV infections and possible cancers increases with a combination of serological tests of multiple virus proteins. Hence, using both oncoproteins yields positive immunological results with samples from cervical cancer patients.

The main method for public health screening for cervical cancer has been the Papanicolaou smear. For a variety of reasons, the Papanicolaou smear is less than an ideal screening test. Drawbacks include difficulty of obtaining samples, high rate of false negatives (up to 20%), and requirements for specialized labs staffed by highly trained personnel. Nucleic acid methods have been developed, but are not ideal primarily due to their high cost and like requirement for highly trained personnel. Another assay is the so-called "DNA Hybrid Capture". This method suffers from high cost and sampling difficulties. What is needed is a low cost, simple, sensitive and specific assay that can be performed on readily obtainable bodily samples.

An object of the invention is to develop antibody active peptides derived from the HPV E2 protein and the HPV 16 and 18 E6 and E7 oncoproteins. It is a further object to provide these peptides in a chemically pure form. It is a still further object to provide a simple, rapid, less expensive and more sensitive test for diagnosing not only HPV infections, but also most, if not all, HPV associated neoplasms. A further object is to provide antigens for use in HPV inoculums that will induce antibody production and killer T cell activity.

SUMMARY OF THE INVENTION

The above stated objects and other objects of the invention are accomplished by novel peptides, the sequences of which were derived by the inventor from careful analysis of the early coding regions of the E2, E6, and E7 oncoproteins of HPV 16 and 18. The peptides lend themselves to a highly sensitive and specific diagnostic immunoassay. Antibodies to the E2 oncoprotein are found in those infected with HPV. Antibodies to the E6 and E7 oncoproteins are found in those with HPV associated neoplasms. The peptides of the invention, ranging in size from about 19 amino acid residues to about 30 amino acids can readily be synthesized by chemical means and obtained at purities that can exceed 99%. Although the peptides could be obtained by other means, in their pure form there may be a much reduced likelihood for undesirable cross reactivity with random antibodies. Hence, the pure peptides of the invention lend themselves to diagnostic immunoassays of high specificity. The diagnostic immunoassay method comprises taking a sample of body fluid or tissue likely to contain antibodies, if present, reacting it with one or more of the peptides of the invention, then assaying for the presence of an antibody-peptide reaction.

Immunoassays employing peptides derived from the E2 region serve as reliable indicators that HPV infection has or has not occurred. Immunoassays employing the peptides derived for the E6 and E7 oneoproteins serve as reliable indicators that HPV associated malignancy or premalignant cell transformation has taken place. One of the most useful aspects of the invention is in diagnosing cervical carcinoma, both squamous cell and adenocarcinoma as well as any epithelial cell abnormality associated with oncogenic HPV infection including koilocytosis; hyperkerotosis; precancerous conditions encompasssing intraepithelial neoplasias or intraepithelial lesion; high-grade dysplasias; and invasive or malignant cancers. Besides cervical cancer, detection of antibodies to peptides derived from the HPV E6 and E7 oncoproteins is useful for detecting head and neck cancers, small cell lung cancers, penal and anal squamous cell carcinomas, and melanoma.

DESCRIPTION OF THE DRAWINGS

The invention will be described in more detail below, reference being made to the accompanying drawings in which:

FIGS. 5 and 6 are a table showing the results of a diagnostic immunoassay on controls and patients with HPV infection and HPV associated neoplasms.

DETAILED DESCRIPTION OF THE PREFERRED EMBODIMENT

The peptides of the invention are derived from the early coding regions of the E2, E6, and E7 oncoproteins of HPV 16 and 18. The derivation of the peptides of the invention were based on their predicted ability to react with antibodies formed in a host infected with oncogenic HPV. Among the specific factors used in the selection process is solubility in aqueous solution or hydrophilic nature. It was assumed that hydrophilic regions of the oncogene product protein were more likely oriented toward the surface of the complete protein under natural conditions, and that such are consequently antigenic regions against which antibody reactivity would most likely occur.

Another factor included having a single lysine or cysteine near the N-terminus. By near, it is meant at the terminus or no more than two residues from the terminus. By single, it is understood that additional lysine or cysteine residues are at least eight residues from the N-terminus. It is preferable that lysine or cysteine be added to the N-terminus of a reactive peptide, if such a residue were not already at or near the N-terminus. It is also preferable that an overall relative paucity of cysteine residues in the amino acid sequence be maintained. Also preferred was an overall paucity of tryptophan and methionine residues and a relative abundance of glycine or asparagine residues. By paucity, it is meant that there are as few occurrences as possible and by abundance, it is meant that there is no limit on the number of occurrences in the sequence. A still more preferred embodiment of the peptide compositions includes up to six additional amino acid residues attached to the carboxy terminus where those residues are any combination of glycine and asparagine. Additional glycines and asparagines orient the peptide in the aqueous reaction medium in a fashion that increases antibody binding.

Figure 1:
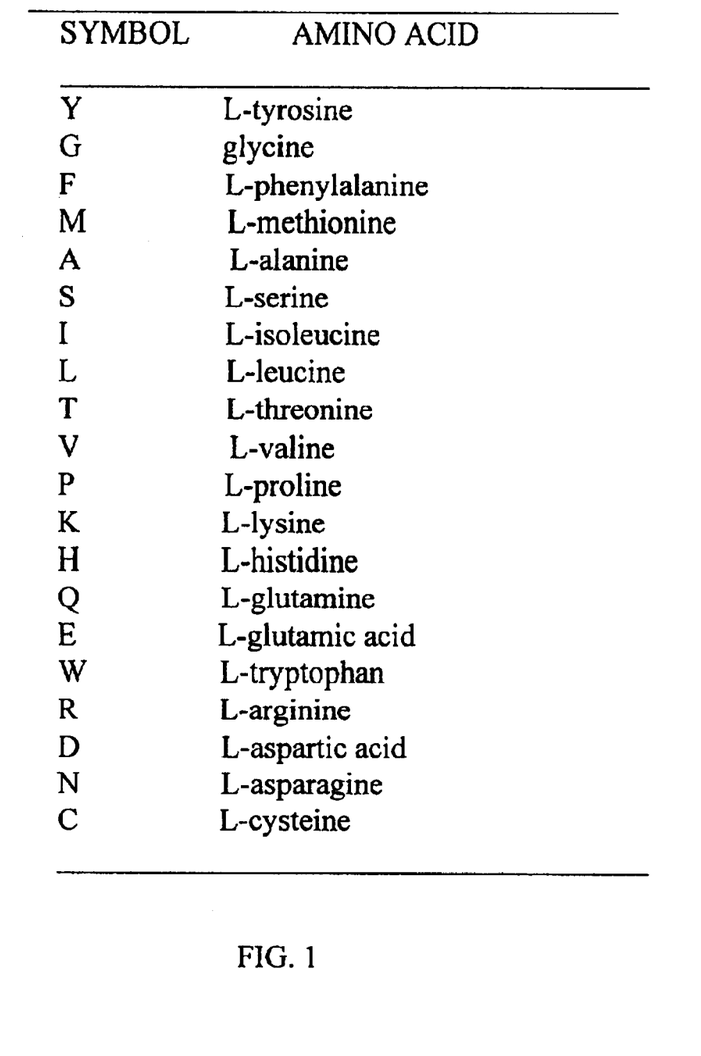
FIG. 1 is a table showing the single letter code used for the corresponding amino acid used in the FIGS. 2–4.
Figure 2:
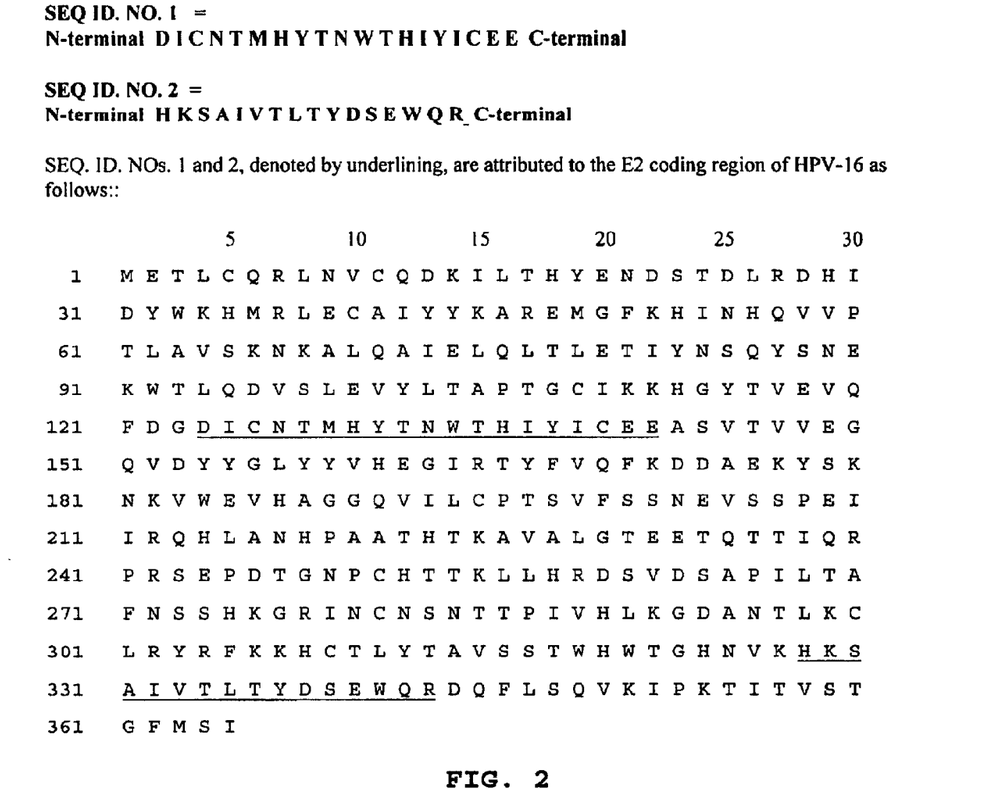
FIG. 2 is a coded depiction of the early coding region of the E2 oncoprotein wherein SEQ NO 1 and SEQ NO 2 of the invention are underlined.
Figure 3:
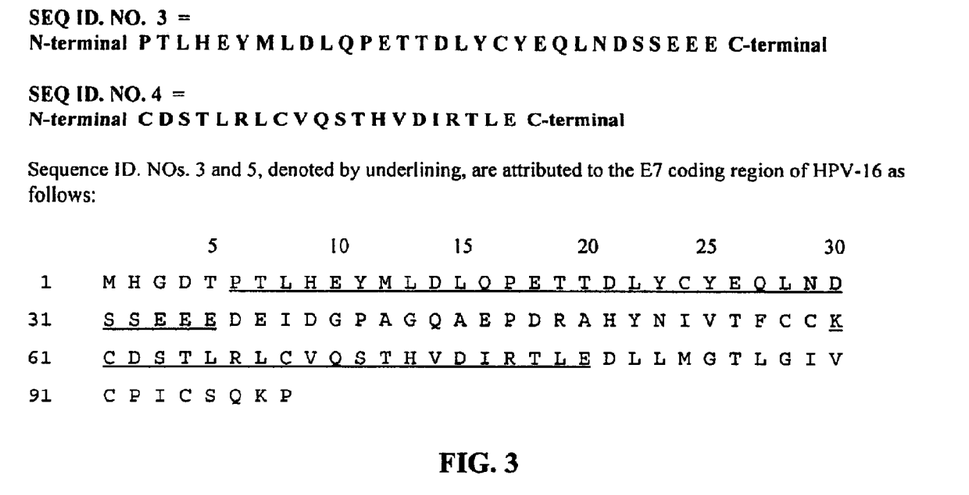
FIG. 3 is a coded depiction of the early coding region of the E6 oncoprotein wherein SEQ NO 3 of the invention is underlined.
Figure 4:
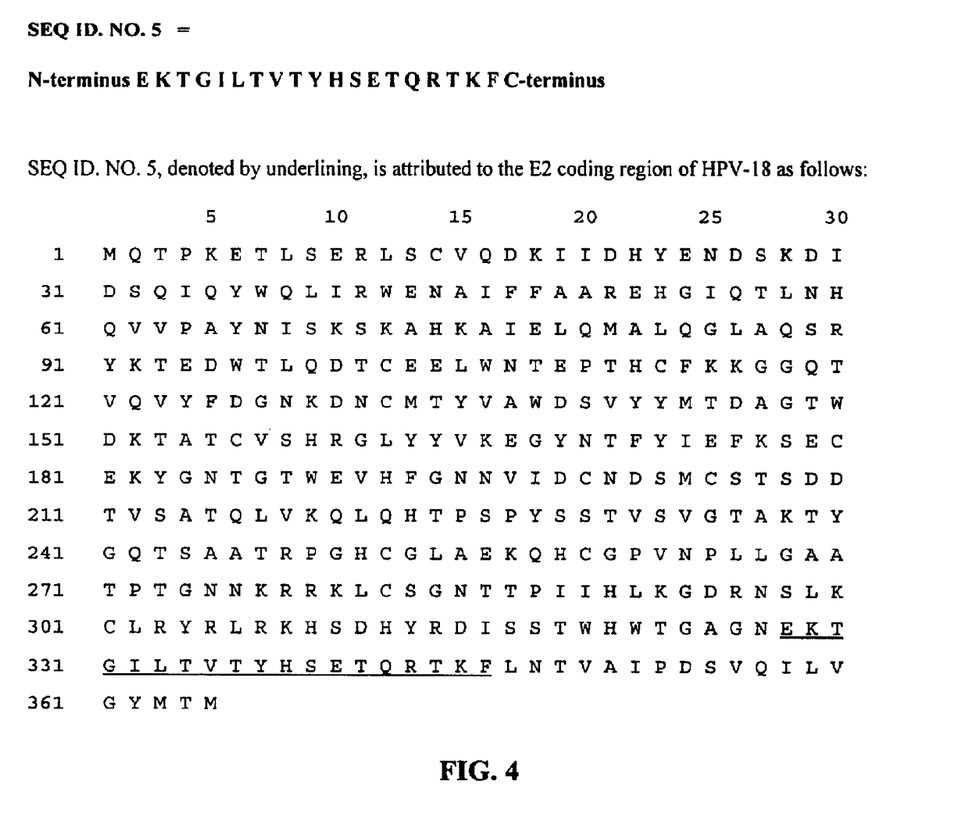
FIG. 4 is a coded depiction of the early coding region of the E7 oncoprotein of HPV 18 wherein SEQ NO 5 of the invention is underlined.

FIGS. 2–4 disclose five specific peptide sequences ranging from 16 to 30 residues. The key to the coded sequences in FIGS. 2 through 4 is given in FIG. 1. As depicted in FIG. 2, SEQ NO. 1 and NO. 2 were derived from the E2 Region of HPV 16. Decoded and using the standard three letter abbreviations sequence, numbers 1 and 2 are as follows:

```
                                           (SEQ. NO. 1)
Asp Ile Cys Asn Thr Met His Tyr Thr Asn Trp Thr
1               5                   10

His Ile Tyr Ile Cys Glu Glu
       15
```

-continued (SEQ. NO. 2)
His Lys Ser Ala Ile Val Thr Leu Thr Tyr Asp Ser
1               5                   10
Glu Trp Gln Arg
        15

Sequences number 3 and 4 are derived from the E7 early coding region of HPV 16 as depicted in FIG. 3. Decoded using the standard three letter abbreviations sequence number 3 is as follows:

(SEQ. NO. 3)
Pro Thr Leu His Glu Tyr Met Leu Asp Leu Gln Pro
1               5                   10
Glu Thr Thr Asp Leu Tyr Cys Tyr Glu Gln Leu Asn
        15                  20
Asp Ser Ser Glu Glu Glu
25              30

(SEQ. NO. 4)
Cys Asp Ser Thr Leu Arg Leu Cys Val Gln Ser Thr
1               5                   10
His Val Asp Ile Arg Thr Leu Glu
        15              20

Sequence number 5 is derived from the E2 early coding region of HPV 18 as depicted in FIG. 3. Decoded using the standard three letter abbreviations sequence number 5 is as follows:

(SEQ. NO. 5)
Glu Lys Thr Gly Ile Leu Thr Val Thr Tyr His Ser
1               5                   10
Glu Thr Gln Arg Thr Lys Phe
        15

The use of the peptides in a diagnostic method is based on the fact that antibodies to the native epitopes of the E2, E6, and E7 oncoproteins of HPV 16 and 18 are found in those suffering from a variety of HPV associated epithelial cell abnormalities ranging from mere infection to malignancy. More particularly, such HPV associated cellular abnormalities may include, but are not limited to, koilocytosis; hyperkerotosis; precancerous conditions encompassing intraepithelial neoplasias or intraepithelial lesions; high-grade dysplasias; and invasive or malignant cancers. The malignant neoplasms associated with HPV are discussed above. The method comprises taking a sample of body fluid or tissue likely to contain antibodies. This sample is preferably easy to obtain and may be serum or plasma derived from a venous blood sample. However, cervical secretions, cervical tissue, tissue from other body parts, or other bodily fluids are known to contain antibodies and may be used as a source of the patient sample. Once the peptide antigen and sample antibody are permitted to react in a suitable medium, an assay is then performed to determine to presence of an antibody-peptide reaction.

Synthesis of the Peptide Sequences

While the peptides of the invention could be obtained by a variety of prior art methods, among them recombinant sources, chemical synthesis is the preferred method as it facilitates accumulation of a sizable amount of peptide in a substantially pure form, around 99% by weight in the present case. The synthesis of peptides was done on a 0.25 scale using (9-fluorenyl)methoxycarbonyl (FMOC)-protected L-amino acids, with super acid-labile 2-chlorotrityl resin (Novabiochem, Nottingham, UK) as a solid support. Resin preloaded into a reaction vessel was washed with dimethyl formamide and then drained completely. To this resin was added 10 ml of 20% piperidine in dimethyl formamide. The mixture was then shaken for 5 minutes and drained. Another 10 ml of 20% piperidine in dimethyl formamide was added, and the mixture shaken for 30 minutes. After draining, the resin was washed with dimethyl formamide four times, and then once with dichloromethane. The resin beads were considered appropriately prepared if these turned blue using the standard ninhydrin test.

For each amino acid, coupling solution was prepared: 1 mmol Fmoc Amino Acid of choice; 2.1 ml 0.45 M 2-(1H-benzotriazole-1-yl)-1,1,3,3-tetramethyluronium-hexafluoro-phosphate/hydrobenzotriazole [1 mmol]; 348 $\mu$l of N,N-diisopropylethylamine [2 mmol]. The mixture was shaken for a minimum of 30 minutes. The reaction vessel was drained, the resin washed four times with dimethylformamide, and a final time with dichloromethane. A standard ninhydrin test was performed to ascertain coupling of the amino acid. For each amino acid, coupling solution was added to the resin in the appropriate order, with the coupling reaction repeated until all amino acids were in place along the peptide.

The completed peptide was cleaved from the resin by reaction for two hours with a solution of 5% $H_2O$, 5% phenol, 3% thioanisole, 3% ethanedithiol, 3% triisopropylsilane, 81% trifluoroacetic acid. After cleavage, the resin mixture was filtered into cold methyl-tbutyl-ether. The precipitated peptide was then washed twice with cold methyl-tbutyl-ether and dried under gaseous nitrogen. The molecular weight of the peptide was checked by Matrix-Assisted laser Desorption Time-of Flight Mass Spectrometry, and the purity by High Performance Liquid Chromatography using a C18300A 5 $\mu$ column. The synthesized peptide sequences were at a 99% level of purity, but it is emphasized that lesser levels were still considered possibly appropriate for assay purposes.

Storage of the Amino Acid Sequences

The manufactured amino acid sequences were suspended in PBS at pH 7.0 to a concentration of 1 mg/ml. The sequence solutions were split to 500 $\mu$g peptide per tube and storage was done at −20° C.

Maleic Anhydride Binding of the Amino Acid Sequences to Titer Plates

REACTI-BIND™ Maleic Anhydride Activated Polystyrene Plates (Pierce, Rockford, Ill.) were employed. Each amino acid sequence was diluted to 12.5 $\mu$g/ml with coating buffer (100 mM sodium bicarbonate buffer, pH 9.4). To each titer well, 100 $\mu$l (1.25 $\mu$g) of the diluted sequence solution was added. The plate was then incubated for one hour at room temperature with shaking. The plate was emptied and residual liquid tapped onto a clean paper towel. Each well was washed with 100 $\mu$l wash buffer (0.1% bovine serum albumin and 0.05% Tween-20 in phosphate buffered saline, pH 7.0). This was repeated for a total of three times. Each time, the plate was emptied and residual liquid tapped onto a clean paper towel. To each well, 200 $\mu$l of blocking solution (3% bovine serum albumin and 0.05% Tween-20 in phosphate buffered saline, pH 7.0) was then added. Blocking solution was left in each well for one minute. The titer plate was then emptied by inversion. Filling with blocking solution and emptying was done three times. Finished titer plates were dried at room temperature and stored at 4° C. for up to four months.

Sample Collection

All samples were taken from female patients during their scheduled visits for gynecological examinations. Cotton swabs were used to obtain endocervical cells. Cells for the ThinPrep Pap smear (Cytyc Corporation, Stamford, Conn.) were dispersed in ThinPrep preservative solution. Cells for the HPV DNA Hybrid Capture assay (Digene Corporation, Silver Spring, Md.) were suspended in the same medium. Both the ThinPrep Pap smear and the HPV DNA Hybrid Capture assay are further elucidated below.

Venous blood was obtained by usual phlebotomy methods, with a 21- or 22-gauge double-pointed needle into a agar barrier tube. A total of 7–9 ml blood was taken from each subject. After allowing 15 minutes at room temperature for clot formation, the blood was centrifuged for 15 minutes. Serum was aspirated away from the cells, using a disposable pipette, dispensed into Eppendorf tubes as 0.25-ml aliquots, and stored at –80° C.

Immunoassay

As a negative control, serum had been obtained from virgin females, ages 14 and 15. Subject and control sera were diluted 1:25 with wash buffer (0.1% bovine serum albumin and 0.5% Tween-20 in phosphate buffered saline, pH 7.0). To each well, 100 $\mu$l of diluted serum was added, and the assay plate incubated for one hour at room temperature with shaking. Each well was then rinsed three times, each with 200 $\mu$l wash buffer. Each rinse was for five minutes. The plate was emptied each time by tapping residual liquid onto a clean paper towel.

To each well was added 100 $\mu$l horseradish peroxidase conjugated-mouse-anti-human IgG diluted 1:8000 with wash buffer. The assay plate was then incubated for 1 hour at room temperature. Using multiple pipettes, each well was rinsed with 200 $\mu$l wash buffer four times. Each rinse was for five minutes. Before each rinse, the plate was emptied and residual liquid tapped on a paper towel.

To each well was added 100 $\mu$l 3,3',5,5' tetramethylbenzidine, a substrate for horseradish peroxidase. This was incubated at room temperature until a visually obvious green-blue color developed, 5–30 minutes, and the reaction stopped by placing 150 $\mu$l 1.5 M $H_2SO4$ into each well.

Comparisonal Tests—ThinPrep Pap Test and HPV DNA Hybrid Capture

ThinPrep Pap Test—Cleared as a replacement for the conventional Pap smear, the ThinPrep Pap Test overcomes the limitations of the conventional method. By improving the way the sample slide is prepared, the ThinPrep Pap Test actually improves the quality of the test. In clinical trials, the ThinPrep Pap Test improved the detection of low-grade and more severe lesions by 65% in screening populations and by 6% in high-risk populations. Its use also reduced the number of less-than-adequate specimens by more than 50%. Hence, the ThinPrep Pap test was used here to optimize the results from cervical cytology.

Rather than smearing the cervical sample onto a slide as is done with the conventional Pap smear, the cervical swab was rinsed in a vial of preserving solution. The specimen was sent to a certified clinical laboratory, where an instrument, the ThinPrep 2000 processor, was used to disperse and filter the contents to reduce blood, mucus, and inflammation. A thin, even layer of the cervical cells was then mechanically deposited onto a slide, the result being a uniform preparation of well-preserved cells ready for precise microscopic examination. Slides were microscopically examined and interpreted by a board certified gynecological cytologist.

Hybrid Capture II HPV DNA Testing—The Hybrid Capture II HPV DNA test (HC II, Digene Corporation, Silver Springs, Md.) was employed as a comparison to the ELISA test with peptides of the invention. It is approved by the U.S. Food and Drug Administration to test for oncogenic HPV DNA, as reflexive follow-up of an ASCUS (Atypical Squamous Cells of Undetermined Significance) or other abnormal Pap results. The hybrid capture involves a molecular hybridization that uses non radioactive probes with amplification of the detection of the hybrid ones for chemoluminescence. The material for analysis is denatured and reacts with specific genic probe forming hybrid RNA/DNA that are captured by antibodies that cover the walls of the tube. To follow the hybrids immobilized, these are reacted with specific antibodies against RNA/DNA conjugated with alkaline phosphatase. Forming a stable substratum, the hybrids are detected by chemoluminescence via spectometry.

The test was run according to the manufacturer's protocol using the microtiter plate based format and probes for "high carcinogenic risk" HPV types. This was done at the same certified clinical laboratory at which the ThinPrep Pap smear was processed. Human papillomavirus determinations were quantitative, with samples producing readings of 1 or more times the positive control (1 pg/mL HPV DNA or 5000 HPV genome copies per test) considered to contain virus DNA.

Visualization/Interpretation of Completed ELISA Tests

The bottom of the titer plate was cleaned with 70% ethanol, and the titer plate loaded into the Plate Reader.

Absorbance was read at 450 nm, with 100 ml of TMB solution plus 100 ml of 2N HCl used as a blank control. The wells marked A1 & A2 were used to assess background (A1, A2).

Results

Figure 5:
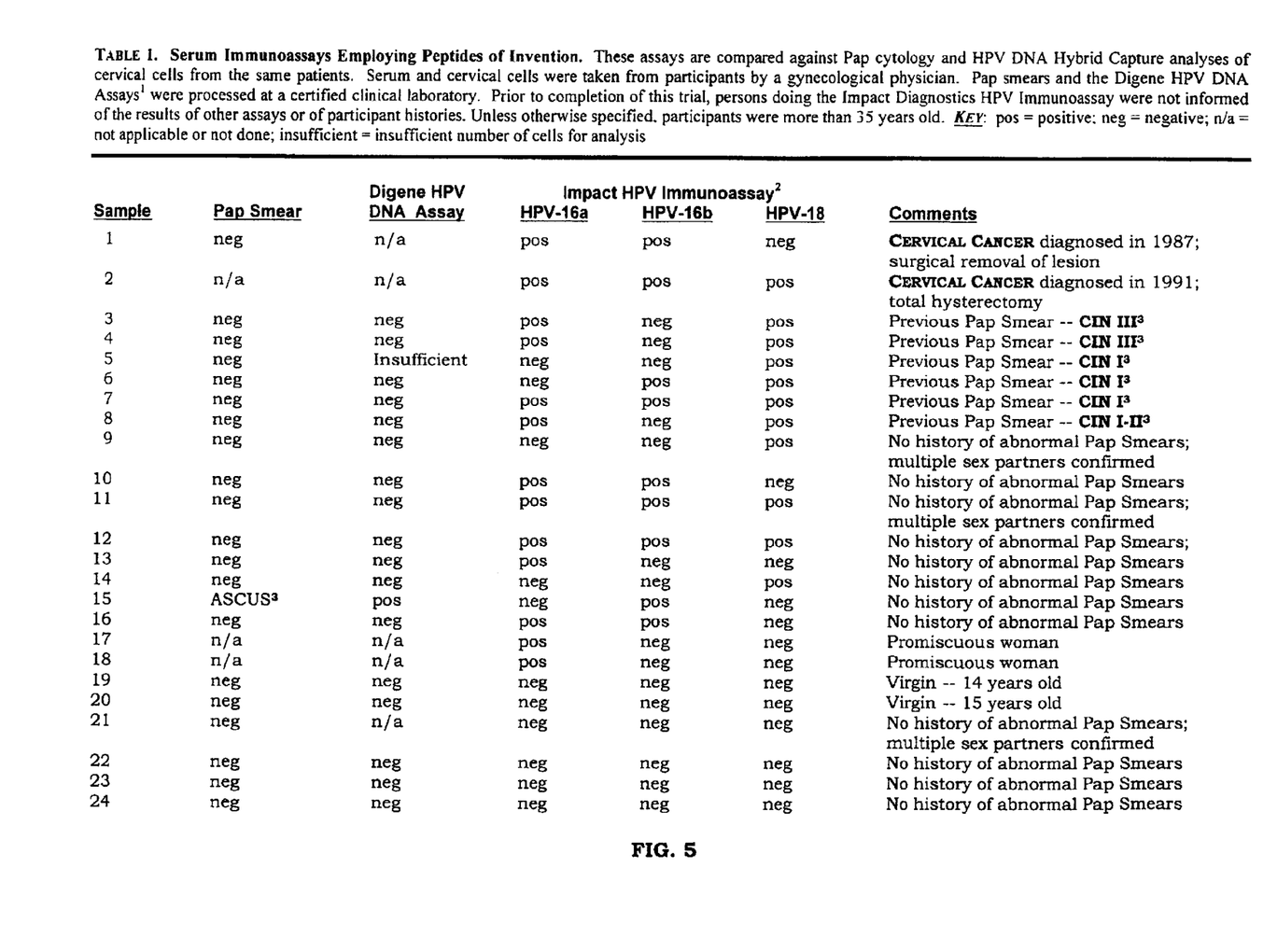

The results comparing Pap smear, Digene HPV DNA assay, and immunoassay according to the invention are given in Table 1 shown in FIGS. 5 and 6. Thirty one subjects were tested. Samples 19 through 31 were from women with a low pre-test probability by virtue of sexual history and/or prior Pap smears and results were negative in all samples for all tests actually performed. This indicates a low rate of false positives and a high negative predictive value.

Samples 1 through 18 were from women with a high pre-test probability by virtue of proven clinical/pathological history or a sexual history of multiple partners. In all of these samples at least one immunoassay performed according to the invention was positive. This indicates a high positive predictive value. Since in some cases only one of the three immunoassays was positive, the value of employing the combination of peptides is demonstrated. The low false positives and high true positives indicates a test of high sensitivity and high specificity.

Also worth noting is that patient 1 had pathology proven adenocarcinoma of the cervix. Patient number 2 had squamous cell carcinoma of the cervix.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

More particularly, the various changes that may be made were summarized in U.S. Pat. No. 5,629,146 to Dillner, et al., who said:

"By showing that a peptide is immunoreactive, the inventors have defined that it contains an epitope reactive with human sera. The epitope contained within this peptide sequence is not absolutely dependent on the exact sequence of the peptide, but can also be contained in a variety of minor modifications of the original peptide. Such modifications include extensions, truncations, cyclizations and amino acid substitutions. Sometimes the question arises if such a modified peptide should be considered a new peptide containing a new epitope. By competitive immunoassays with the original peptide and the modification thereof, it is straightforward to determine if the modified peptide is substantially immunoreactive with antibodies to the original peptide and thus contains the same epitope. It should be emphasized that a peptide can be produced in many different ways. Herein peptide synthesis by organic chemistry methods has been used, but the same peptides can also be produced by many other means for example by recombinant DNA expression systems.

It is understood that the herein contained description of the methods is intended to exemplify, but not limit, the present invention. An immunoassay can for example be performed in a variety of different ways. Detection of the antibodies that have bound to the specific antigen can for example be achieved with various antibodies to antibodies (anti-antibodies) or other compounds with affinity for antibodies, such as protein A or protein G. These reagents can be labelled in many different ways, for example radioactively (radioimmunoassay), with fluorescein (fluoro immunoassay) or enzymatically (enzyme-linked immunoassay, ELISA or EIA). A special case of enzymatic immunoassay is when the antigen-antibody complexes are detected on tissue sections. Such a procedure is instead referred to as immunostaining or immunohistocytochemistry, although the underlying principle is the similar as for ELISA.

An ELISA procedure can also be carried out in a variety of formats. Methods for enhancement of ELISA sensitivity using several layers of anti-antibodies, avidin-biotin complexes and enzyme-anti-enzyme antibody complexes are well known in the art. The solid support for fixation of antigen is usually plastic, as described here, but a variety of other solid supports such as latex or agarose have been described. It is also not necessary for the antigen to be directly fixed onto the solid support. There is for example a commonly used ELISA format that fixes the specific antigen to the solid support via a solid-phase-fixed antibody to the antigen, so-called catching antibody ELISA or sandwich ELISA. A special case of immunoassay which involves a blotting (transfer) of antigen to a solid support in sheet format is termed immunoblotting. Typically, the solid support is nitro-cellulose or nylon sheets, but other supports have been described. It is also a typical feature of this method that, prior to blotting, the antigens are separated according to size by gel electrophoresis or similar methods. Detection of antibodies bound to the specific antigen on the sheet can be carried out in similar ways as for other immunoassays. The here described detection using an anti-antibody, a biotin-avidin complex enhancement step and an enzymatic labelling is just one example of such a detection.

For diagnostic methods in general it is well known that a combination of several diagnostic methods produces a diagnostic method with better sensitivity and/or specificity than the individual tests contained in the combination. It is self-evident that any of the here described antibody tests could be combined with each other, or with other tests, to produce a combined diagnostic test with optimal sensitivity and specificity."

I claim:

1. An immunoassay method for detecting infection in a human by human papillomavirus 16, said method comprising the steps of:

reacting a sample of body fluid or tissue likely to contain serum antibodies raised against a polypeptide which includes amino acids 124 through 142 of the Eb2 early coding region of human papillomavirus 16 with a peptide according to SEQ ID NO.: 1, wherein carboxymethylcysteine is substituted for one or more cysteine residues in said peptide; forming a complex of said peptide and sample serum antibodies, wherein the formation of said antibody-peptide complex confirms the presence of serum antibodies to human papillonia-virus 16; and detecting said antibody-peptide complex.

2. An immunoassay method for detecting infection in a human by human papillomavirus 16 according to claim 1, wherein the detection step is accomplished by means of visual inspection of a color change.

3. An immunoassay method for detecting infection in a human by human papillomavirus 16 according to claim 1, wherein the detection step is accomplished by a spectrophotometer.

4. An immunoassay method for detecting infection in a human by human papillomavirus 16 according to claim 1, wherein the detection step further comprises inspecting said antibody-peptide complex for physical-chemical changes.

* * * * *

UNITED STATES PATENT AND TRADEMARK OFFICE
CERTIFICATE OF CORRECTION

PATENT NO. : 6,743,593 B2
DATED : June 1, 2004
INVENTOR(S) : Yao Xiong Hu

It is certified that error appears in the above-identified patent and that said Letters Patent is hereby corrected as shown below:

Column 3,
Line 14, please delete "active", please insert therefore -- reactive --.
Line 50, please delete "oneoproteins", please insert therefore -- oncoproteins --.

Column 13,
Line 40, please delete "of the Eb2", please insert therefore -- of the E2 --.
Line 46, please delete "antibodies, wherein", please insert therefore -- antibodies; wherein --.
Lines 48-49, please delete "papilloniavirus", please insert therefore -- papillomavirus --.

Signed and Sealed this

Eighth Day of February, 2005

JON W. DUDAS
*Director of the United States Patent and Trademark Office*